(12) United States Patent
Avila

(10) Patent No.: US 10,719,930 B2
(45) Date of Patent: Jul. 21, 2020

(54) AUTOMATED SCAN QUALITY MONITORING SYSTEM

(71) Applicant: ACCUMETRA, LLC, Clifton Park, NY (US)

(72) Inventor: Ricardo S. Avila, Rexford, NY (US)

(73) Assignee: ACCUMETRA, LLC, Clifton Park, NY (US)

( * ) Notice: Subject to any disclaimer, the term of this patent is extended or adjusted under 35 U.S.C. 154(b) by 141 days.

(21) Appl. No.: 15/566,191

(22) PCT Filed: Apr. 13, 2016

(86) PCT No.: PCT/US2016/027331
§ 371 (c)(1),
(2) Date: Oct. 12, 2017

(87) PCT Pub. No.: WO2016/168328
PCT Pub. Date: Oct. 20, 2016

(65) Prior Publication Data
US 2018/0096477 A1    Apr. 5, 2018

Related U.S. Application Data

(60) Provisional application No. 62/146,886, filed on Apr. 13, 2015.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/5258* (2013.01); *A61B 6/583* (2013.01);
(Continued)

(58) Field of Classification Search
None
See application file for complete search history.

(56) References Cited

U.S. PATENT DOCUMENTS 7,068,751 B2  6/2006  Toth et al.
7,372,988 B2  5/2008  Yoakum-Stover et al.
(Continued)

OTHER PUBLICATIONS

PCT/US2016/027331, International Search Report and Written Opinion, dated Jul. 21, 2016.

*Primary Examiner* — Soo Jin Park
(74) *Attorney, Agent, or Firm* — George A. Leone; Citadel Patent Law

(57) ABSTRACT

A method for calculating and reporting image quality properties of an image acquisition device after a subject or object has been scanned consists of a scan quality monitoring system with automated software for receiving scans and radiation dose data from scanners and automated algorithms for analyzing image quality metrics and radiation dose tradeoffs. Image quality assessment methods include algorithms for measuring fundamental imaging characteristics, level and type of image artifacts, and comparisons against large databases of historical data for the scanner and protocols. Image quality reports are further customized to report on expected clinical performance of image detection or measurement tasks.

13 Claims, 5 Drawing Sheets

(51) Int. Cl.
*A61B 6/00* (2006.01)
*A61B 6/03* (2006.01)
*G06T 1/00* (2006.01)

(52) U.S. Cl.
CPC ............ *A61B 6/586* (2013.01); *G06T 1/0007* (2013.01); *G06T 7/0002* (2013.01); *A61B 6/037* (2013.01); *A61B 6/5294* (2013.01); *A61B 6/542* (2013.01); *G06T 2207/10072* (2013.01); *G06T 2207/20* (2013.01); *G06T 2207/30168* (2013.01)

(56) References Cited

U.S. PATENT DOCUMENTS

| | | |
|---|---|---|
| 8,333,508 B2 | 12/2012 | Reiner |
| 8,355,551 B2 | 1/2013 | Thielemans et al. |
| 8,538,776 B2 | 9/2013 | Reiner |
| 2010/0310146 A1 | 12/2010 | Higgins et al. |
| 2011/0211743 A1* | 9/2011 | Avila ................ G06T 7/0016 382/131 |
| 2011/0270053 A1 | 9/2011 | Larson |
| 2013/0195255 A1 | 1/2013 | Avila et al. |
| 2013/0100345 A1 | 4/2013 | Yan et al. |

\* cited by examiner

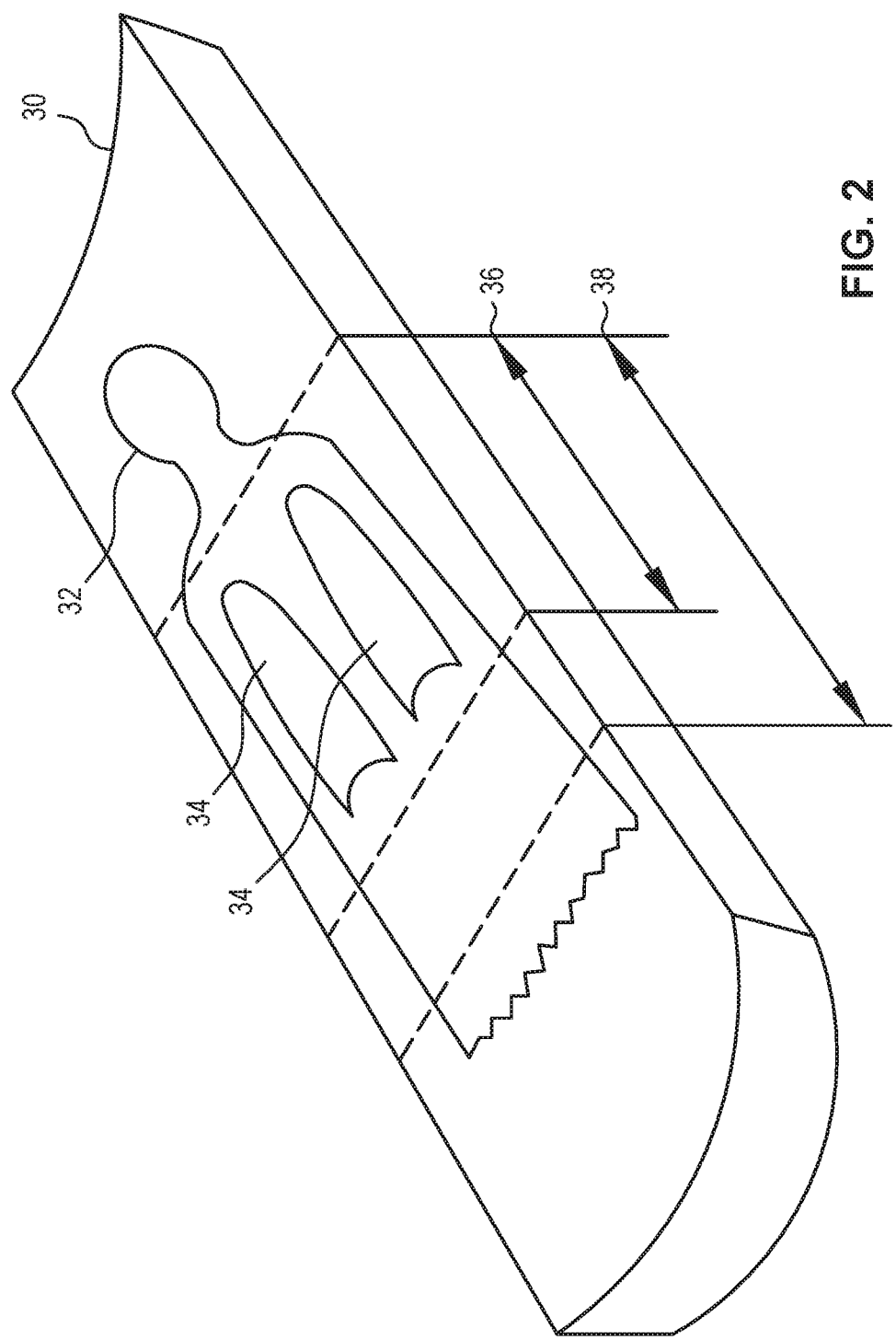

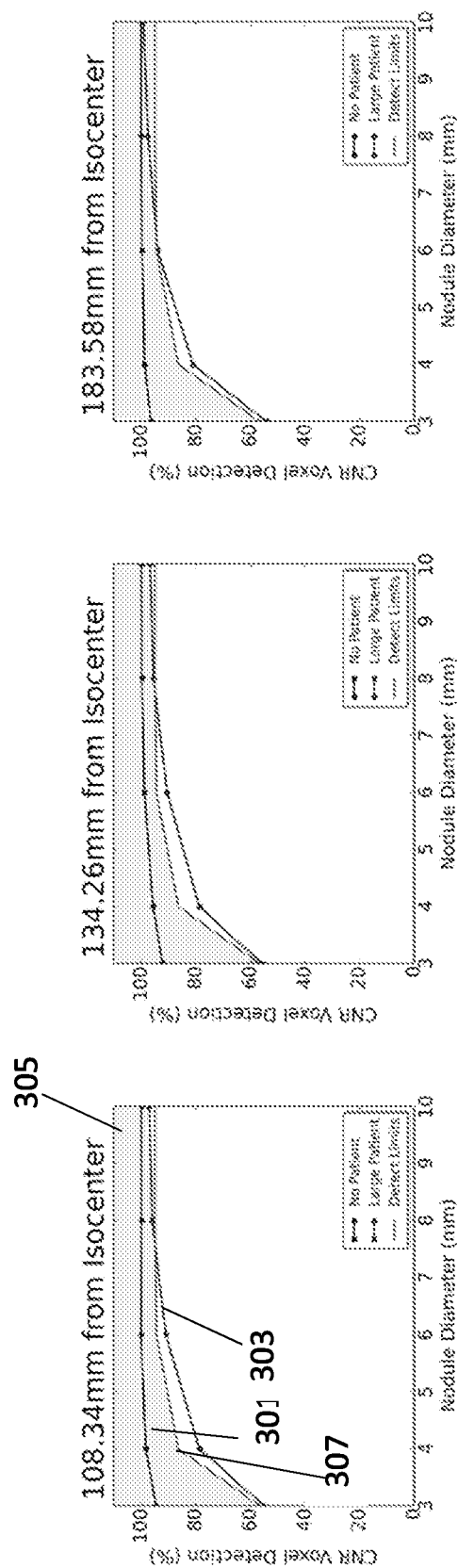

AUTOMATED SCAN QUALITY MONITORING SYSTEM

CROSS REFERENCE TO RELATED APPLICATIONS

This patent application claims the benefit of U.S. Prov. Ser. No. 62/146,886 filed Apr. 13, 2015 entitled "Automated Scan Quality Monitoring System," which is incorporated by reference herein.

BACKGROUND

Field of the Invention

The present invention relates to the automated assessment of the quality of scanner acquired images for performing a set of decision making tasks including but not limited to detection and measurement of health conditions and diseases.

Description of the Related Art

Three dimensional image acquisition devices, such as CT, XR, PET/CT, MRI, and Ultrasound scanners, are routinely used to non-invasively obtain structural and functional information on the internal condition of subjects and objects of study. Imaging studies produced by scanners are typically performed to make decisions on life threatening conditions and circumstances. It is therefore critical to ensure that the imaging data upon which the decisions are made have sufficient image quality for the tasks being performed.

Institutions conducting imaging studies rely on two main methods for maintaining sufficient image quality. First, image acquisition devices are regularly assessed with radiological quality assurance devices that can flag when a number of individual image quality issues are present. Current image acquisition calibration phantoms contain individual components for measuring specific imaging characteristics, including resolution, noise properties, and expected signal intensity verification (e.g. CT linearity). Several calibration assessment procedures are typically needed to perform these assessments, some that are done on a daily basis and others that are done at weekly or longer intervals. These procedures have traditionally been performed with manual image measurement methods. More recently there has been a trend to automate these image quality assessment procedures, but visual inspection of phantom images remains part of the protocol. Second, individuals that interpret scanner acquired images, such as radiologists, are required to assess the quality of the acquired images for the specific set of tasks being performed (e.g. detection of cardiac calcification, monitoring of lesion size change). Given that the human visual system is particularly adept at detecting issues and anomalies, this type of image quality assessment can catch many subtle issues. However, human visual inspection is both subjective and qualitative leading to high variability in image quality assessment, particularly for newer and more computational image measurement tasks. More importantly, reviewer subjective assessment lacks the analytical precision needed to ensure that more advanced image based measurement and detection algorithms will perform sufficiently.

Image acquisition modalities subject patients and objects of study to radiation and/or substances that can be harmful and damaging to human health. For example, Computed Tomography scanners use the attenuating properties of ionizing x-ray radiation as the fundamental basis for image formation. As a result, several important quality characteristics of a CT image are proportional to the type and amount of x-ray radiation administered during the scanning process. CT image noise levels and linearity properties are particularly dependent on the level of x-ray tube current and voltage used. A fundamental tradeoff exists between the amount and type of radiation administered and the quality of a CT image.

Over the last decade there has been increasing awareness and emphasis on reducing CT imaging study radiation dose to as low as reasonably achievable (ALARA). Radiologists and technologists must determine the lowest level of radiation to administer during an image study to obtain 3D images needed for clinical decision making. CT scanners provide individual radiation dose reports for each scan performed providing much needed radiation dose information for optimization. Scanners also store scan protocol information typically by the type of imaging study and measurement procedure being performed. However, there are no reports available for the resulting image quality of a scan and analytic tools with which to optimize radiation dose and image quality are missing from the available toolset. Radiologists and technologists must again rely on visual inspection and subjective methods to determine if image quality and radiation dose are being sufficiently optimized for the patients that are being scanned. This is further complicated by the fact that patient characteristics (e.g. size) and numerous scanner settings and options (e.g. prescribing the scanning region) can have a significant impact on radiation dose and image quality.

Another challenging aspect of image quality and dose optimization is that there are now numerous new and complex software applications that are being relied upon to measure medical imaging data including lesion volume change, CT perfusion, and PET tracer uptake. Determining the optimal tradeoff between radiation dose settings for the patient and image quality needed when advanced 3D algorithms are being used to arrive at clinical decisions far exceeds the capabilities of an individual radiologist or technologist.

Another related area in need of image quality assessment is in clinical trials that involve imaging to measure clinical trial endpoints. Large multi-center clinical trials often use numerous clinical sites with a wide range and diversity of scanning equipment in order to obtain the statistically necessary number of patients. Many clinical trials include secondary endpoints that involve advanced 3D measurements. Verification of image quality in these trials is typically done by the two main methods outlined above, periodic calibration of scanners and visual inspection of acquired studies. Here again there is a need for more quantitative and analytical tools for verifying that image quality was sufficient for a clinical study.

A co-pending patent application on a new type of radiological quality assurance device was filed on Apr. 13, 2015 as U.S. Provisional Patent Application No. 62146542, entitled "TABLE TOP IMAGE CALIBRATION PHANTOM," to the inventor herein. That disclosure is incorporated herein by reference and describes a locally thin calibration device layer addition to a scanner table such that every scanned 3D image will contain a comprehensive set of image quality reference objects. Another type of small calibrated phantom, referred to as a pocket phantom, also contains precision manufactured image quality reference objects in a small package that can be placed on or near the patient. Automated software can be used to detect the table top device or the pocket phantom device in the scanned images, analyze the image at the phantom location, and produce a fully automated image quality report.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

In one embodiment, a scan quality monitoring system automatically receives scans from an image acquisition device, analyzes the anatomy and structures in the scan including pocket phantoms or table phantoms, and produces a quantitative image quality report.

In another embodiment, the scan quality monitoring system receives images and corresponding radiation dose reports from an image acquisition device, analyzes the combination of anatomy, phantom data, and radiation dose to calculate a quantitative metric representing the tradeoff between radiation dose and image quality.

In another embodiment, CT scans are analyzed to determine whether the target anatomy was obtained or whether additional anatomy was obtained leading to increased radiation dose. The scans are also analyzed to determine if resolution was compromised by the improper setting of the scan field of view acquisition parameter or the setting of table height.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 2 illustrates an example of a CT table acquiring CT image slices of the lungs of a patient for the task of detecting early lung cancer in a screening setting.

FIG. 3A-FIG. 3C chart estimated solid lung nodule detection performance of the scanner/protocol combination at different distances from scanner isocenter, corresponding to targets consisting of phantoms (e.g. rolls of tape) that were successfully found and measured.

Figure 1:
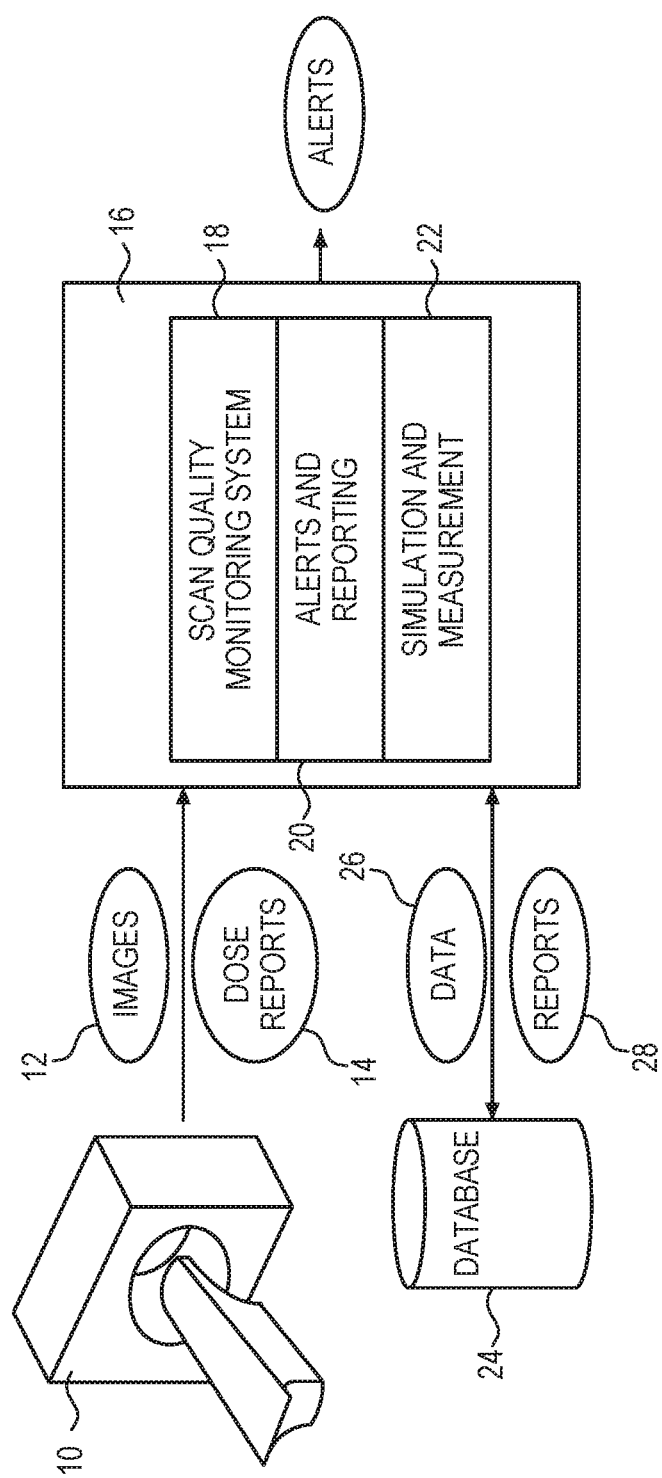
FIG. 1 shows an example of an automated scan quality monitoring system.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes an automated image quality monitoring system. Several features of methods and systems in accordance with example embodiments are set forth and described in the figures. It will be appreciated that methods and systems in accordance with other example embodiments can include additional procedures or features different than those shown in the figures. Example embodiments are described herein with respect to measuring scanner properties. However, it will be understood that these examples are for the purpose of illustrating the principles, and that the invention is not so limited. Additionally, methods and systems in accordance with several example embodiments may not include all of the features shown in the figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

References to algorithms refer to generally available scanning, measurement and segmentation algorithms as known by those skilled in the art unless otherwise specified. Examples of such algorithms are described in U.S. Pat. No. 9,033,576, issued May 19, 2015 and entitled "Medical Imaging System for Accurate Measurement Evaluation of Changes in a Target Lesion," which is incorporated herein by reference.

As mentioned in the background section, image quality assessment is typically performed between patient scans, and despite the recent introduction and use of some automated methods, image quality assessment still relies heavily on the subjective expertise and knowledge of the individuals performing the evaluation. This has resulted in the potential for some patients to receive poor quality scans in between calibration tests and greater imaging variability than necessary for many 3D measurement and detection tasks involving analytical software.

This method takes the concept of automated image quality analysis further by continuously performing image quality measurement for each scan and providing individuals interpreting the images (e.g. radiologists) and organizations responsible for monitoring the scanning (e.g. study sponsors, CROs, scan registries) with new forms of quantitative image quality data appropriate for understanding the performance of image detection and measurement tasks with the acquired images. These new image quality analyses and reporting methods include automatically analyzing each acquired image and:

a) Producing a quantitative report on image quality which may include new measures such as expected task performance for a set of image-based tasks and whether sufficient image quality was obtained given these new metrics.

b) Also analyzing available radiation dose information to quantitatively report on the trade-off between image quality and radiation dose and whether the tradeoff was sufficient to meet required ALARA guidelines and task requirements.

c) Reporting on specific opportunities to achieve a better tradeoff between image quality and radiation dose if adjustments are made to the image acquisition protocol or a different scanner and protocol is used.

Each of these new quantitative image quality analysis and reporting areas is further described below.

Referring now to FIG. 1, an example of an automated scan quality monitoring system is shown. An automated scan quality monitoring system 16 receives acquired images 12 and corresponding radiation dose reports 14 from at least one scanner 10. The scan quality monitoring system 16 analyzes each study dataset received to calculate image quality metric data 26 and image quality reports 28 which are stored with other datasets in a central database 24. A reporting and alert subsystem 20 sends out alert reports when image quality metrics or image quality and radiation dose tradeoffs do not achieve required levels. An optional simulation and measurement system 22 generates clinically relevant expected performance data for clinical tasks that need to be performed with the acquired image data 12.

Referring now to FIG. 2, an example of a CT table acquiring CT image slices of the lungs of a patient for the task of detecting early lung cancer in a screening setting is illustrated. A CT table 30 acquires CT image slices of a clinical target, such as, for example, lungs 34 of a patient 32 for the task of detecting early lung cancer in a screening setting. If the desired region to be scanned 36 is exceeded and additional anatomy is obtained 38, the patient 32 will receive more radiation dose than recommended for this screening study, proportional to the length of over scanning. The automated scan quality monitoring system, as shown in FIG. 1, determines whether scan image quality and radiation dose are optimized and reports on the findings. The report includes suggestions for reducing radiation dose and maintaining sufficient image quality and points out that radiation dose can be lowered if the scan acquisition extent were made to only contain the lungs of the patient.

Automated Reports on Image Quality

Image data from a scanner is transferred automatically to the scan quality monitoring system which then analyzes the scan data and determines the types of calibration and measurement reference data available. Automated scan quality reports can be generated on any combination of the following data:

i) Regions of the scan containing pocket phantom quality assurance devices.

ii) Regions of the scan containing a table phantom quality assurance device.

iii) Regions of the scan containing known objects and signal properties such as identifiable anatomic regions and homogeneous object regions (e.g. blood in the aorta) including air regions (e.g. air in the trachea).

One example of the image quality monitoring system disclosed herein establishes a new way of measuring image quality of each scan. One useful approach is to first use a combination of a calibration phantom(s) (either a table phantom or recent small disc shaped phantom scans with a specific scan protocol) and image-derived quality metrics from the patient scan (e.g. noise measurements in air regions) to estimate the fundamental image quality characteristics of an individual scan across the full reconstructed field of view (because these values change even within an image).

The next step is to translate these fundamental image quality properties (which describes the image formation process and can be compactly represented with a simple mathematical equation) into clinical task performance measures such as lung nodule detection performance or lung nodule change measurement performance. Fundamental image quality characteristics are obtained and a large simulation is performed to create numerous simulated images of the clinical target(s) and surrounding structures in question (e.g. a solid lung nodule surrounded by a lung parenchyma pattern). The simulation must allow for typical variation present in a scan such as small changes in position and orientation of objects as well as fluctuations in linearity, resolution, noise, artifacts, etc. Once tens, hundreds or thousands of simulated images are obtained a measurement algorithm is employed to measure each target object within each image. By measuring all of the simulated images the expected distribution of a specific measurement(s) including the bias and variance of the measurement can be obtained. Similarly, the simulated images can be used to evaluate the performance of other clinical tasks like detection of a lesion. Note that the simulated images can be generated to account for the impact of different size patients or different materials within a patient (lots of contrast).

Presented here for the first time are (a) the ability to obtain a small set of fundamental performance characteristics across the full scanner field of view for a CT scanner and scan protocol combination (spatial resolution, sampling rate, noise, linearity, spatial warping, temporal resolution, multiple energy response/linearity, . . . ) and (b) the ability to translate these fundamental properties into expected clinical task performance for a range of clinical task targets using a large and very fast simulation and measurements of all simulated images.

Once the fundamental properties of the image are in hand (for example, CT linearity, 3D PSF, sampling rate, image noise, spatial warping) and a geometric description of a target object (including its position, orientation, and internal and external signal intensities) the main elements needed to create a simulated image are available. This is done by first creating a blank 3D image with an observed sampling rate in the real image and just large enough in all three dimensions to hold a selected target object in any orientation. Next the 3D PSF of the scanning system is convolved with the target geometric object at every voxel in a simulated image, allowing for small deviations in position on and orientation in the voxel grid, just as there is no sub-voxel guarantee of position and orientation when doing real world imaging with a scanner. Representing the target object in a much higher resolution binary mask image allows for convolution with an image representation, which is easier to do than with geometry. When assigning intensities to the outside and inside of the geometric object the CT linearity curve should be consulted, allowing for small deviations as before, so that the simulated image has similar linearity biases as the original image. Given that a 3D PSF can be represented well with a 3D Gaussian and convolution with a Gaussian is separable, the computational time to produce a basic image of the target object is greatly reduced. If a spatial warping model is available, then it can be applied during or after the convolution step. The resulting simulated image now has the basic signal intensities of the imaging system represented with the fundamental image properties described above.

A final step is to add in models for noise and any other image formation artifacts represented with a fundamental property extracted from the original image. For example, addition of Gaussian noise, again with small deviations as is present in real-world scanners, is fast, efficient and can provide the needed intensity variability to obtain a first order simulation of the imaging system, but other noise models may be more appropriate and can be substituted. Each time this simulation is run a slightly different image will result due to the small variations present in the position, orientation, intensities, etc. of the target object.

To better understand the performance of a real world imaging system scanning a geometric object, the simulation should be run 10s to 1000s of times. Then for each simulated image the performance of a clinical task with the simulated image can be evaluated. For example, it may be desirable in some cases to know the bias and variance of performing volumetric measurements on different size lesions, which can be represented as an ellipsoid. To understand this a large simulation with 6 different size ellipsoids can be run to generate 150 simulated 3D images for each ellipsoid size. Next, a lesion segmentation algorithm can be applied to each simulated image to obtain the measured volume of the target object in the simulated image. Analyzing the mean and standard deviation of the simulated image measurements provides a first order estimate of the bias and variability typically expected in an image formation system with the fundamental properties that have been utilized.

Estimated performance of other clinical tasks can also be evaluated with the same simulated images. Continuing the example, the same set of simulated images can be analyzed for determining how detectable an object is with the image properties we have obtained from the real world image. A complex computer aided detection algorithm can be applied to the simulated image to see if the object is able to be detected or a simple contrast to noise ratio (CNR) metric can be applied to the exact voxels within the target object to see if the CNR of the target object within a simulated image is within a detectable range. Once a large set of simulated images representing the image formation process of an imaging system is obtained, virtually any algorithm (representing, for example, a clinical task) can be applied to all images to obtain a first order estimate of the performance of the imaging system and the algorithm combination.

In one example, when a pocket phantom is located in the scan a set of fundamental image quality characteristics can be obtained including signal strength for different materials, 3D PSF or resolution, distance measurement performance, noise properties, and types and levels of image artifacts. Information on spatially varying properties can also be presented if multiple pocket phantoms are present. This quantitative image quality information can be reported directly as individual measurements and also further analyzed to produce more advanced clinical task performance reports.

In another example, when a table phantom quality assurance device is present within the scan data all of the information discussed above for a pocket phantom can be evaluated and reported as well as more detailed information on spatial image quality variation within the scan. In particular, the presence of periodic spatial warping can be measured using a table phantom containing a grid pattern.

If a radiological quality assurance phantom is not present with the patient during scanning, there remain numerous opportunities to measure image quality. The air in the trachea and the blood in the aorta of a CT scan can be automatically detected and analyzed for image noise properties. The transition from soft tissue and skin to surrounding air can be analyzed with modeling constraints to estimate scanner resolution. These same skin boundary regions as well as the diaphragm region can be analyzed to detect and quantitatively measure motion artifacts. One approach to measuring motion in CT images is to determine if the expected resolution at a boundary is observed or is compromised by motion artifacts.

Numerous additional image quality measurements can be computed by analyzing scanner images and their image header information. One is whether the CT scan table was positioned so as to center the patient in the acquired images. Many CT properties such as resolution, CT linearity, and noise properties can vary considerable as a function of distance from scanner iso-center. It is therefore important to ensure that the CT table is always set appropriately for the scan purpose (e.g. early lung cancer detection). The anatomy to be imaged can be segmented from the acquired image and the point representing the average center of mass of the image slices can be compared to the iso-center position. The distance between the two 2D points can be reported and if it exceeds an institution's standards, an alert (e.g. email or test message alert) can be generated. In addition, the reconstruction field of view (in the X, and Y scanner dimensions) should be set such that the primary anatomic regions needed for the scan utilize the full available field of view. In CT there are typically only 512×512 pixels available for producing a single slice or image. Setting the scan field of view too small will result in missed anatomy. Setting the scan field of view too large will result in poor sampling of the anatomy and will degrade detection and measurement performance. All of these image-based quality metrics can be measured, reported, and monitored quantitatively.

If a comprehensive set of image quality properties is obtained such that a mathematical model of the image acquisition system can be constructed with high confidence, then additional and more advanced image quality measures can be computed. This approach uses an image simulator to create numerous simulated images of virtual anatomy models, with additional modeling of variation present in scans such as the sub-voxel position of the anatomy. These simulated images are then measured for clinical task performance which may include the bias and precision of one-dimensional, two-dimensional, or three-dimensional measurements. The name and identifying information for stored acquisition protocols permits an automated algorithm to always know the clinical tasks that need to be performed and the imaging scenarios that need to be evaluated (e.g. CT pulmonary embolism detection is mainly a low contrast detectability task). Similarly, boundary bias and precision of volumetric measurements can be estimated with this approach. Advanced measures and metrics can also be evaluated with this approach resulting in estimates of bias and precision for such advanced measures as Agatston calcification scoring or CT perfusion measures. The main advantage of this approach is that it translates image quality performance data into the clinical performance data that radiologists can understand and readily interpret.

Automated Reports on the Image Quality and Radiation Dose Tradeoff

All of the above image quality measures can be analyzed, before or after scanning, with respect to the reported radiation dose for the acquired scan. If patient weight and BMI is available to the scan quality monitoring system, the resulting image quality performance measures can be plotted against the provided radiation dose level and compared to a database of comparable scans for a scanner and a comparably sized patient. When the obtained radiation does not obtain minimum levels of image quality the issue is noted and the institution alerted.

Minimization of radiation dose can also be evaluated by verifying that only the necessary anatomy was imaged for the scan. For example, if a scan of the thorax is needed for early lung cancer detection screening then acquiring large sections of additional anatomy beyond the upper and lower extent of the lungs will expose the patient to more radiation than is necessary. A radiation dose measurement can be obtained by automatically identifying the anatomy to be imaged and determining if the scan extent far exceeds this anatomical region. In addition, the same automated method can also determine if the scan extent did not capture the entire anatomical region.

Automated Reports on Opportunities to Improve Image Quality and Radiation Dose

Quantitative reports on the tradeoff between image quality and radiation dose would provide a more objective and reliable method for achieving ALARA. However, it is also important to know what to consider if image quality is considered too low or radiation dose is considered too high. Advanced scan quality correction reports can analyze the available image metrics, radiation dose obtained or predicted, and suggest effective ways in which to improve the resulting image quality and radiation dose tradeoff. This can be achieved by analyzing a large database of historical tradeoff data to find scan protocol modifications that are known to result in better tradeoff performance. In addition, known fundamental relationships between scan parameters and radiation dose can also be used to guide institutions on ways to improve the expected tradeoff.

Using the automated scan quality system herein, image quality reports are generated to provide all of this information in an easy to use format for clinicians. One example report starts with data that the CT scanner was programmed to provide (in some cases this may be different from actual results) and then follows with graphs showing the expected performance of doing different clinical tasks with that specific scanner/protocol combination. The example report provides expected solid lung nodule detection performance as well as change measurement performance for six different nodule diameter sizes and three positions within the scanner field of view. To aid the physician a green area is provided outlining the minimum expected performance of the scan for a clinical task (this is a paradigm shift that will require the field to establish minimum performance thresholds for each clinical task that a scan is expected to support). If the expected performance plots of a scan do not appear in the minimum performance green region, then the scan is considered to have missed its performance target. The report ends with a listing of the fundamental performance characteristics of the scanner/protocol combination. This helps explain why a clinical task performed as it did and is highly technical/mathematical in nature. This section contains information that is more important for a medical physicist than a clinician.

EXAMPLES

An assessment of scanner image quality was performed Using a 3D CT DICOM Series Found to Contain 3 Rolls of 3M ¾ Inch×1000 Inch Scotch Magic Tape® 810. The scanner and protocol settings were as in Table I below.

Table I
Scanner and Protocol
Manufacturer: GE MEDICAL SYSTEMS Tube kVp: 120.00
Scanner Model: LightSpeed VCT Tube mAs: 25.00
Scanner Station: GEVCT2 Slice Thickness: 1.25
Study Date: 20160331 Slice Spacing: 1.250
Recon Kernel: LUNG Pitch: 0.98
Iterative Settings Radiation Dose:
Sampling Rate: 0.941×0.941×1.250 mm
Volume Size: 512×512×67 mm
Study Description:
Series Description: 1.25 lung
Series Instance UID: 1.2.3.4
Directory Name: s1
Image Quality Analysis Status
Slice thickness and spacing were found to be within acceptable limits for this analysis (2.5 mm).

Referring now to FIG. 3A-FIG. 3C, estimated solid lung nodule detection performance of the scanner/protocol combination at different distances from scanner isocenter, corresponding to each roll of tape that was successfully found and measured is charted. Within each chart there are two plots shown. Referring particularly to FIG. 3A, the top line 301 indicates how detectable five different lung nodule diameters would be using the currently measured scan properties, where no patient is on the table. The lowest line 303 indicates how detectable the same five lung nodules would be if a large patient were being scanned with similar resolution and other image properties as measured in this image acquisition. The shaded region 305 indicates the level of detection performance a protocol should attain. Detection limits are indicated by line 307. The other graphs follow the same general format. The graphs show varying distances from isocenter including 108.34 mm (FIG. 3A), 134.26 mm (FIG. 3B) and 183.58 mm (FIG. 3C).

Figure 4A:
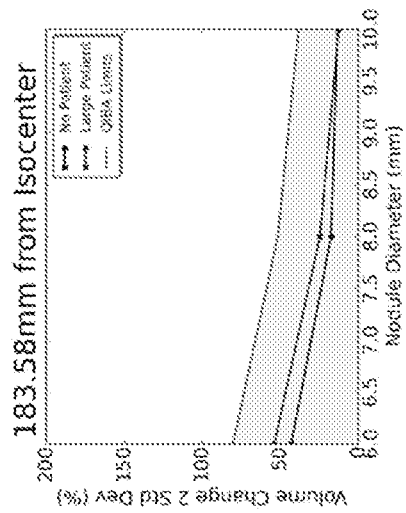
FIG. 4A-FIG. 4C, chart estimated solid lung nodule volume change measurement performance of the scanner/protocol combination at different distances from scanner isocenter, corresponding to targets consisting of phantoms (e.g. rolls of tape) that were successfully found and measured.
Figure 4B:
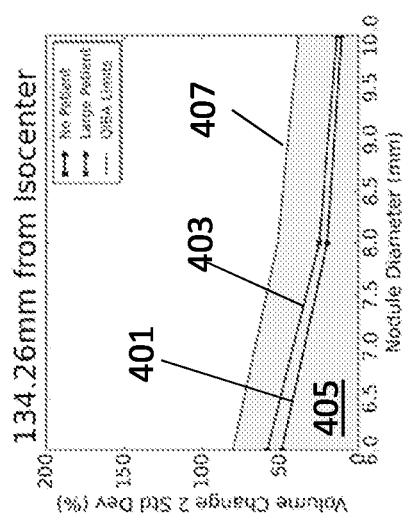
Figure 4C:
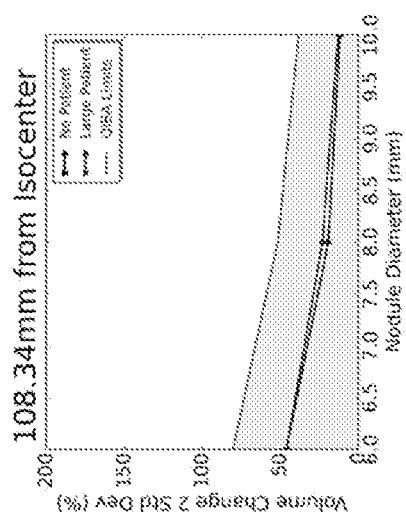

Referring now to FIG. 4A-FIG. 4C, the estimated solid lung nodule volume change measurement performance of the scanner/protocol combination at different distances from scanner isocenter, corresponding to each roll of tape that was successfully found and measured is charted. Within each chart there are two plots shown. Referring particularly to FIG. 4B, the generally lowest line 401 indicates how much volumetric change measurement error, expressed as a percent of a ellipsoidal volume, can be expected at three different lung nodule diameters using the currently measured scan properties, where no patient is on the table. The middle line 403 indicates how much volume change measurement error to expect for the same three lung nodule sizes, but now with a large patient in the scanner. The shaded region 405 indicates the QIBA defined level of change measurement performance a protocol should attain. Detection limits are indicated by line 407. The other graphs follow the same general format. The graphs show varying distances from isocenter including 108.34 mm (FIG. 4A), 134.26 mm (FIG. 4B) and 183.58 mm (FIG. 4C).

Figures 5A, 5B, 5C:
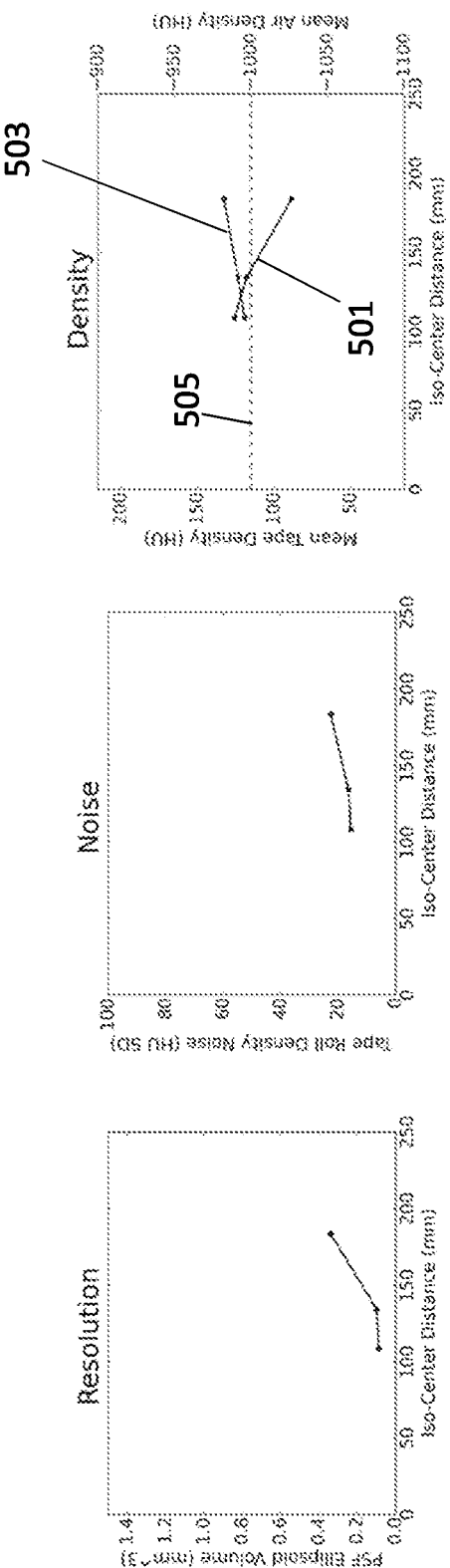
FIG. 5A shows the 3D resolution of a scan acquisition at different distances from scanner isocenter.
FIG. 5B charts the level of noise at different distances from scanner isocenter.
FIG. 5C shows a plot of the deviation of the phantom material mean air density (HU) from expected and the deviation of air density from expected.

Referring now to FIG. 5A, the 3D resolution of the scan acquisition at different distances from scanner isocenter is summarized. Referring now to FIG. 5B, the level of noise at different distances from scanner isocenter is graphically shown. Referring now to FIG. 5C, a plot of the deviation of the tape material mean air density (HU) from expected plotted as line 501 and the deviation of air density from expected plotted as line 503 is shown. Ideally the line 501 and the line 503 would overlap the broken line 505 indicating the expected HU values for the two materials. Customized reports with additional quantitative image quality metrics can be provided using the automated system disclosed herein as well as automated image quality reports for additional modalities including XR, PET/CT, MRI, and US. The other graphs follow the same general format.

Clinical Task Performance Predictor

The system as described above can estimate clinical task performance for standard objects, as for example, an ellipsoid shape that represents a solid lung nodule. However, actual nodule presentation can be far more complicated with multiple internal components, attachment to multiple structures, and potentially being surrounded by additional medical conditions (e.g. a atelectasis). An estimate of clinical task performance of an ellipsoid will not fully capture the bias and variance of performing on these more complex and varied lesions. So the next step is to take one or more scans and corresponding segmentations of the clinical target(s) (e.g. actual nodules) and surrounding structures and create multiple simulated images with these more complex models. Then a measurement or detection method is applied to the simulated images to arrive at the expected measurement performance of the clinical task. Because a target model derived from the real patient scan is being used, with all of its patient specific complexity, a much better estimate of clinical task performance can be obtained.

The steps involved to realize the innovation in the last paragraph are to:
 a. Obtain one or more scans of calibrated objects (discs, or table phantom) before or during a scan of the patient.
 b. Extract or estimate fundamental performance measures (ideally for the full field of view) of one or more patient scans that were done to achieve one or more clinical tasks. This step can be done with any combination of prior calibration data, recent calibration scans (discs or table phantoms or other phantoms), patient data features extracted from the image(s), and historical data of that type of scanner and protocol (stored in a database).
 c. Extract one or more clinical target models (geometric structure, intensity, etc.) from a patient scan representing a clinical target and surrounding environment. For example, a clinical target model could be a part-solid nodule attached in a specific geometry to several vessels surrounding it. Here a nodule segmentation algorithm may be used and high resolution label masks created for different structures in the image, like the location of the solid components, the part solid components, the surrounding lung parynchema, local vasculature, and any other large structures.
 d. Numerous instances of simulated images containing the specific patient clinical target models (and optionally standard objects like spheres and ellipsoids) are created allowing for variation present in all scans (e.g. different noise distributions, small variations in resolution, small variations in linearity).
 e. An algorithm is applied to each simulated image to obtain measurements and statistics for the resulting performance of that algorithm on the specific clinical target models. For example, a lung nodule segmentation algorithm can be applied to all of the simulated images to see how much bias and variance is present in measuring volumes with the scanner and protocol. Since masks for the different structures in the clinical target are available, performance for each mask can be evaluated.
 f. The clinical task performance across all of the simulated images can be analyzed to arrive at estimates of clinical task performance for standard geometric shapes and/or the scanner/protocol/patient/object specific clinical structure or target. This information can also be provided on displays and reports.

Once the scanner/protocol/patient/object specific estimates of bias and variance for a specific clinical task are obtained, it can be used to better manage a patient. For example, after detecting a suspicious lung nodule an important clinical task becomes the amount of time and the quality of a follow up scan needed to determine if the suspicious nodule is growing, staying stable or shrinking. Ideally the next scan should be performed as soon as possible, but the error associated with the current scan and the expected error in the follow-up scan will limit how soon that scan can be done. Of course, the patient wants to know as soon as possible as well without resorting to a potentially dangerous procedure, like a lung biopsy, to obtain a quick answer.

The next innovation is to mathematically predict the minimum amount of time needed to reliably determine (e.g. with 95% confidence) changes in size or density of an object. From statistical literature it can be shown that a change in volume from V1 at time point 1 and V2 at time point 2 needs to exceed the interval $\pm 1.96 \times \sqrt{([V_1 \times CV_1]^2 + [V_2 \times CV_2]^2)}$ at time point 2, where $CV_1$ and $CV_2$ represent the coefficients of variation of the imaging and measurement system at each time point. Thus if one wishes to distinguish a malignant growth rate of a lesion with 180-day doubling time from a slowly growing lesion with a 400-day doubling time, the minimum time needed for follow-up would be determined when the computed intervals no longer overlap. This approach for determining follow-up times applies to measurement of change in any object or clinical target in any modality including lung nodules, lesions, masses, emphysema, airway wall thickness, bone density, cardiac calcifications, cartilage thickness, brain structures, PET lesions, etc. These computed recommendations, particularly on the quality of a scan or a follow up scan, can be verified with disc, table, or other phantoms.

Similarly, the scanner/protocol/patient/object specific quality of clinical detection tasks can be better determined given one or more scans and can provide guidance to the patient/clinician for the quality and follow-up interval needed for the scans. The management of a patient for a detection task needs to also be scanner/protocol/patient/object specific and take into account variance from all sources. For example, if a patient is determined to be at high risk for fast growing lung cancer and therefore high vigilance is needed, specific guidance can be provided to the patient/clinician on the scan quality and interval of scanners and protocols needed for the specific patient.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

What is claimed is:

1. A method for automated image quality analysis, comprising:
 operating a scanner for scanning a region of interest to acquire image data where the region of interest includes anatomy and a calibrated phantom device;

continuously performing quantitative image quality measurements on the acquired image data that includes imaged anatomy data and imaged phantom device data;

receiving radiation dose reports from the scanner, where the radiation dose reports include radiation dose information;

calculating a quantitative metric representing a tradeoff between the radiation dose information and the quantitative image quality measurements;

determining calibration and reference data from the acquired image data;

estimating fundamental image quality characteristics from the calibration and reference data;

using the estimated fundamental image quality characteristics in an image simulator to create a set of simulated images of virtual anatomy models; and measuring the set of simulated images for clinical task performance including include bias and precision of linear, two-dimensional, or three-dimensional linear measurements.

2. The method of claim 1 wherein providing image quality measurement data includes:

reporting on selected opportunities to achieve an improved tradeoff between image quality and radiation dose if adjustments are made to the image acquisition protocol or a different scanner and protocol is used.

3. The method of claim 1 further comprising calculating a quantitative metric on acquired image data including one or more of known objects anatomic regions, homogeneous object regions and air regions.

4. The method of claim 1 further comprising:

locating the phantom device in the region of interest; and obtaining a set of fundamental image quality characteristics selected from the group consisting of signal strength for different materials, 3D PSF or resolution, distance measurement performance, noise properties, and types and levels of image artifacts.

5. The method of claim 4 further comprising reporting information on spatially varying properties if more than one phantom device is present.

6. The method of claim 1 further comprising measuring the presence of periodic spatial warping where the phantom device comprises a grid pattern.

7. The method of claim 1 where continuously performing quantitative image quality measurements further comprises using air measurements from a patient's trachea and a patient's blood in the aorta of a CT scan.

8. The method of claim 7 further comprising analyzing a transition from soft tissue and skin to surrounding air to estimate scanner resolution; and analyzing a patient's diaphragm region to detect and quantitatively measure motion artifacts.

9. The method of claim 1 further comprising computing additional quantitative image quality measurements by analyzing the acquired image data and its image header information including:

a position of a CT scan table; and resolution, CT linearity, and noise properties as a function of distance from scanner iso-center.

10. The method of claim 1 further comprising:

segmenting an anatomy to be imaged from the acquired image data; and then comparing a point representing an average center of mass of image slices to a point of an iso-center position where a distance between these two 2D points can be reported and if it exceeds predetermined standards, then generating an alert.

11. The method of claim 1 further comprising measuring boundary bias and precise volumetric measurements, and evaluating advanced measures and metrics resulting in estimates of bias and precision for advanced measures including Agatston calcification scoring or CT perfusion measures.

12. The method of claim 1 further comprises adjusting the simulated images for different noise distributions, variations in resolution, and variations in linearity.

13. The method of claim 1 further comprising applying a lung nodule segmentation algorithm to the simulated images to measure the presence of bias and variance in measuring volumes with the scanner and protocol.

* * * * *